US006265627B1

(12) United States Patent
Igumnov et al.

(10) Patent No.: US 6,265,627 B1
(45) Date of Patent: Jul. 24, 2001

(54) PROCESS FOR PREPARING POLYFLUOROAROMATIC COMPOUNDS

(75) Inventors: Sergei Mikhailovich Igumnov, Russian Federation, Moscow, Zelenograd 1445-363; Alexandr Vasilievich Zabolotskikh, Perm, both of (RU)

(73) Assignee: Sergei Mikhailovich Igumnov, Moscow (RU)

( * ) Notice: Subject to any disclaimer, the term of this patent is extended or adjusted under 35 U.S.C. 154(b) by 0 days.

(21) Appl. No.: 09/691,445

(22) Filed: Oct. 18, 2000

(30) Foreign Application Priority Data

Nov. 23, 1999 (RU) .................................. 99125573

(51) Int. Cl.$^7$ .................................................. C07C 22/00
(52) U.S. Cl. ............................................................. 570/147
(58) Field of Search ............................................. 570/147

(56) References Cited

U.S. PATENT DOCUMENTS

| 4,684,734 | 8/1987 | Kaieda et al. | 546/345 |
| 4,927,980 | 5/1990 | Cantrell | 568/937 |
| 5,824,827 | 10/1998 | Bildinova et al. | 570/147 |

FOREIGN PATENT DOCUMENTS

| 2718275 | 11/1978 | (DE) . |
| 0781747 | 7/1997 | (EP) . |
| 2084437 | 7/1997 | (RU) . |
| 678864 | 4/1994 | (SU) . |

OTHER PUBLICATIONS

"Industrial Organofluorine Products" Handbook, Leningrad, Khimiya (1990) pp 329 and 333 (English Translation).
English Translation of Claims for RU 2084437 dated Jul. 20, 1997.
English Translation of Claims for SU 678864 dated Apr. 30, 1994.

Primary Examiner—Alan Siegel

(57) ABSTRACT

A process for preparing polyfluoroaromatic compounds by heating halogen-containing aromatic compounds with alkali metal fluorides in the presence of a catalyst, N,N',N"-hexa-substituted guanidinium halide, in the medium of products of incomplete fluorination of a halogen-containing compound with simultaneous continuous withdrawal of target products by fractionation or distillation.

4 Claims, No Drawings

PROCESS FOR PREPARING POLYFLUOROAROMATIC COMPOUNDS

TECHNICAL FIELD

The present invention relates to the organofluorine chemistry and more particularly to a process for preparing polyfluoroorganic compounds which are used as heat carriers, dielectrics, solvents and stock materials for the synthesis of drugs, pesticides, oils, lubricants, etc, (Industrial Organofluorine Products. A Handbook. Leningrad, Khimiya, 1990, pp. 329, 333 (in Russian)).

BACKGROUND ART

Known in the art is a process for preparing fluoroaromatic compounds by reacting a chloroaromatic compound with potassium fluoride in an aprotic polar solvent (sulfolane) at a temperature of 210° C., as a catalyst use being made of isoalkylpyridinium salts of the formula

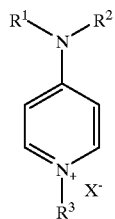

wherein $R^1$ and $R^2$ are monovalent or diva ent radicals selected independently from substituted on unsubstituted hydrocarbon radicals having from 1 to 13 carbon atoms or divalent alkylene radicals capable of forming a cycle containing from 4 to 8 carbon atoms, $R^3$ is a residue of the formula $CH_2C(R^5)HR^4$, $R^4$ and $R^5$=alkyl $C_1$–$C_8$, X=F, Cl, Br (U.S. Pat. No. 4,927,980, C07C 79/12, publ. May 22, 1990). The preferred catalyst is N-(2-ethylhexyl)-4-(N',N'-dimethylamino)pyridinium chloride.

In the description of the process no data can be found on the possibility of preparing highly fluorinated compounds, such as hexafluorobenzene and pentaflorobenzene; examples are presented, illustrating the substitution of only one halogen atom in the aromatic compound. From 4-chloronitrobenzene a mixture is obtained which comprises 48% of 4-fluoronitrobenzene and 45% of 4-chloronitrobenzene. Conversion of 4-chloronitrobenzene is 45%.

The process is disadvantageous in a low yield of target products and using a solvent which must be separated from the reaction products and regenerated.

A process is known for preparing polyfluoroaromatic compounds of the formula $C_6Cl_nBr_mF_p$ (n and m=0–6, p=0–5, n+m+p=6) by reacting a haloaromatic compound with an alkali metal fluoride in the presence of an aminophosphonium catalyst, preferably tetrakis(dialkylamino) phosphonium halides, which is used in an amount of 3–6 mol. % of the molar quantity of the starting haloaromatic compound (U.S. Pat. No. 5,624,827 C07C 25/13, publ. Oct. 20, 1998). The process is carried out in a reactor at a pressure of 5–7 kg/cm² without a catalyst at a temperature of 150–350° C. The total molar yield of hexafluorobenzene and pentafluorobenzene is 70–86% with the hexachlorobenzene conversion of 80–95%.

It is also proposed to carry out the reaction in the liquid phase, for instance, in an aprotic polar solvent or in haloaromatic compounds—dichlorotetrafluorobenzene, trifluorotrichlorobenzene and others, which are in the liquid state at the reaction temperature. In these particular embodiments of the invention with the use of solvents particular examples of preparing fluoroaromatic compounds are not presented.

The process is disadvantageous in the use of a reactor under a pressure, in obtaining a mixture of polyfluorobenzenes instead of one target product, as well as in using catalysts whose synthesis is technologically labor-intensive.

The most relevant technical solution is a process for preparing hexafluoro- and pentafluorochlorobenzenes, which consists in treating hexafluorobenzene with potassium fluoride in sulfolane in the presence of a catalyst, 18-crown-6-macrocyclic polyether. 0.59 mole of the catalyst is used per mole of hexafluorobenzene. The reaction is carried out at a temperature of 180–200° C. for 24 hours. The resulting mixture contains 23–24% of $C_6F_6$, 44–45% of $C_6F_5Cl$ and 30–31% of $C_6F_4Cl_2$. The total yield of hexafluorobenzene and chloropentafluorobenzene as calculated for the charged hexafluorobenzene is 45% (RF Inventor's Certificate No. 676864, C07C$_{25/13}$, publ. Apr. 30, 1994).

The process is disadvantageous in the use of a costly catalyst, in the process being periodic, and in obtaining a mixture of polyfluorobenzenes with a low yield of target products.

DISCLOSURE OF THE INVENTION

An object of the invention is to increase the yield of target products and to simplify the technological process.

Said object is accomplished by heating halogen-containing aromatic compounds with alkali metal fluorides in the presence of a catalyst, N,N',N"-hexa-substituted guanidinium halide, in the medium of products of incomplete fluorination of the starting halogen-containing compound with simultaneous withdrawal of target products by fractionation or distillation.

As the catalyst use is made of N,N',N"-hexa-substituted guanidinium halide of the formula

wherein R—$R^3$=alkyl $C_1$–$C_7$, cycloalkyl $C_5$–$C_8$, aralkyl $C_7$–$C_{12}$; R and $R^1$ and/or $R^2$ and $R^3$ together with the nitrogen atom can form a heterocyclic residue, possibly containing one more heteroatom—oxygen or nitrogen; X=Cl, F, Br, I. Said guanidinium derivatives are described, for instance, in DE 2718275 C07C$_{129/12}$.

PREFERRED EMBODIMENTS OF THE INVENTION

It is preferable to use hexaethylguanidium chloride.

The amount of the catalyst in the reaction is 1–5% by weight of the starting mixture of aromatic compounds. A decrease in the quantity of the catalyst leads to a reduction in the yield of target products, whereas an increase in its quantity over 5% does not produce an essential effect on the process.

The reaction is carried out in the medium of products of incomplete fluorination of starting halogen-containing compounds which are initially charged into a reactor in an amount of 20–50% by weight of the starting mixture of haloaromatic compounds. Henceforth these compounds are constantly present in the process of fluorination as reaction products, and during the in-reactor fractionation they return by gravity into the reactor. This enables one to control the reaction temperature and to make the process continuous.

The synthesis is effected in a reactor provided with a stirrer, the reactor being simultaneously the still of a fractionating column. The process of fluorination is carried out with simultaneous fractionation and withdrawal of the target product found in the reaction zone. When obtaining fluorochloroaromatic compounds whose boiling point is higher than 160° C., withdrawal of the target products is achieved by continuous distillation from the bottom part of the column.

As starting substances for the reaction it is possible to use any aromatic compound which has at least one substitutable halogen atom, except fluorine, in the aromatic ring, e.g., hexachlorobenzene, pentachlorobenzonitrile, trifluoromethyl pentachlorobenzene, etc.

The process of fluorination is carried out with an alkali or alkaline-earth metal fluoride, preferably potassium fluoride in a 1.2–1.4-fold excess from the stoichiometry.

In accordance with the present process there have been prepared, in particular, hexafluorobenzene with the yield of 88.4%, octafluorotoluene with the yield of 92.3%, and other polyfluoroaromatic compounds with a yield not lower than 89%.

The products were analyzed by GLC and NMR-spectroscopy techniques.

The developed process makes it possible to simplify the process technology by excluding the step of purifying the reaction products from the solvent and of regenerating the solvent itself, as well as provides an opportunity for obtaining individual target products (instead of a mixture of polyfluorobenzenes) with a high yield.

The distinctive features of the proposed process are as follows: carrying out the process in the presence of said catalyst in the medium of products of incomplete fluorination of the starting halogen-containing compound with simultaneous continuous withdrawal of target products.

This combination of distinctive features has not been revealed in other technical solutions.

EXAMPLES

The proposed invention will be illustrated by but not limited to the Examples presented hereinbelow.

Example 1

Synthesis of Hexafluorobenzene

The still of a fractionating column, made from steel, having a capacity of 100 dm$^3$, provided with a horizontal scraper-type agitator, with pipes for supplying the starting reagents and for the removal of sludge, is charged with 30 kg of hexachlorobenzene, 2 kg of hexaethylguanidinium chloride, 48 kg of potassium fluoride and 20 kg of a mixture of products of incomplete fluorination of hexafluorobenzene ($C_6F_nCl_m$ where n=1–4, m=5–2). The reaction mixture is agitated at a temperature of 160–170° C., and a fraction with a boiling point of 80–85° C., containing according to the GLC data 91% of hexafluorobenzene and 9% of the mixture of products of incomplete fluorination, is withdrawn from the fractionating column.

17.5 kg of hexafluorobenzene are obtained. The yield of the target product is 88.4% for the starting hexachlorobenzene.

Example 2

Synthesis of Pentafluorochlorobenzane

The process is carried out similarly to Example 1. The reactor is charged with 27 kg of hexachlorobenzene, 1.3 kg of hexathylguanidinium chloride, 37 kg of potassium fluoride and 23 kg of a mixture of products of incomplete fluorination of hexafluorobenzene. The reaction mixture is agitated at a temperature of 165–180° C., and a fraction with a boiling point of 117–118° C., containing according to the GLC data 88% of pentafluorochloroobenzene, 7% of hexafluorobenzene and 5% of the mixture of products of incomplete fluorination, is withdrawn from the fractionating column.

17.5 kg of pentafluorochlorobenzene are obtained. The yield of the target product is 90.7% for the starting hexachlorobenzene.

Example 3

Synthesis of Tetrafluorodichlorobenzene

The process is carried out similarly to Example 1. The reactor is charged with 35 kg of hexachlorobenzene, 1.2 kg of hexamethylguanidinium fluoride, 38 kg of potassium fluoride and 15 kg of a mixture of products of incomplete fluorination of hexafluorobenzene. The reaction mixture is agitated at a temperature of 165–180° C., and a fraction with a boiling point of 150–152° C., containing according to the GLC data 91% of tetrafluorodichlorobenzene, up to 5% of chloropentafluorobenzene and more than 4% of trifluorotrichlorobenzene isomers, is withdrawn from the fractionating column.

24 kg of tetrafluorodichlorobenzene are obtained. The yield of the target product is 89% for the starting hexachlorobenzene.

Example 4

Synthesis of Trifluorotrichlorobenzenes

The process is carried out similarly to Example 1. The reactor is charged with 32 kg of hexachlorobenzene, 1.5 kg of hexaethylguanidinium bromide, 27 kg of potassium fluoride and 18 kg of a mixture of products of incomplete fluorination of hexafluorobenzene. The reaction mixture is agitated at a temperature of 160–175° C., and a fraction with a boiling point of 190–195° C., containing according to the GLC data 81% of a mixture of trifluorotrichlorobenzene isomers, 2–3% of chloropentafluorobenzene and 16–17% of a mixture of dichlorotetrafluorobenzene isomers, is distilled off from the bottom part of fractionating column.

24 kg of trifluorotrichlorobenzene are obtained. The yield of the target product is 90.2% for the starting hexachlorobenzene.

Example 5

Synthesis of Octafluorotoluene

The process is carried out similarly to Example 1. The reactor is charged with 45 kg of trifluoromethyl pentachlorobenzene, 52 kg of potassium fluoride, 2 kg of N,N',N'-tetraethylmorpholino-guanidinium bromide, and 12 kg of a mixture of products of incomplete fluorination of trifluoromethylpentachlorobenzene ($C_6F_nCl_mCF_3$ where n=1–3, m=4–2). The reaction mixture is agitated at a temperature of 160–175° C., and a fraction with a boiling point of 103–105° C., containing according to the GLC data 92% of octafluorotoluene and 8% of products of incomplete fluorination of trifluoromethylpentachlorobenzene, is withdrawn from the fractionating column.

31 kg of octafluorotoluene are obtained. The yield of the target product is 92.3% for the starting trifluoromethylpentafluorobenzene.

Example 6

Synthesis of Pentafluorobenzonitrile

The process is carried out similarly to Example 1. The reactor is charged with 25 kg of pentachlorobenzonitrile, 1.5 kg of N,N,N',N'-tatrapropyl-N"-(N-methylpiperazino)-guanidinium chloride, 35 kg of potassium fluoride and 8 kg of a mixture of products of incomplete fluorination of pentachlorobenzonitrile. The reaction mixture is agitated at a temperature of 165–180° C., and a fraction with a boiling point of 160–163° C., containing according to the GLC data 93% of pentafluorobenzonitrile and 7% of the mixture of products of incomplete fluorination, is withdrawn from the fractionating column.

16.1 kg of pentafluorobenzonitrile are obtained. The yield of the target product is 91% for the starting pentachlorobenzene.

Example 7

Synthesis of Pentafluorobenzene

The process is carried out similarly to Example 1. The reactor is charged with 30 kg of pentachlorobenzene, 2 kg of hexapropylguanidinium chloride, 42 kg of potassium fluoride and 20 kg of products of incomplete fluorination of pentachlorobenzene ($C_6F_nCl_mH$ where n=1–3, m=4–2). The reaction mixture is agitated at a temperature of 175–185° C., and a fraction with a boiling point of 80–82° C., containing according to the GLC data 92% of pentafluorobenzene and 8% or products of incomplete fluorination, is withdrawn from the fractionating column.

18 kg of pentafluorobenzene are obtained. The yield of the target product is 90% for the starting pentachlorobenzene.

Example 8

Synthesis of 1-Trifluoromethyl-2,4,6-trifluoro-3,5-dichlorobenzene

The process is carried out similarly to Example 1. The reactor is charged with 25 kg of trifluoromethylpentachlorobenzene, 19 kg of potassium fluoride, 0.6 kg of N,N,N',N'-tetraethyl-N",N"-dicyclohexylguanidium chloride and 7 kg of products of incomplete fluorination of trifluoronethylpentachlorobenzene. The reaction mixture is agitated at a temperature of 180–190° C., and a fraction with a boiling point of 160–175° C., containing according to the GLC data 95% of 1-trifluoromethyl-2,4,6-trifluoro-3,5-dichlorobenzene, 3% of 1-trifluoromethyl-2,4,5,6-tetrafluoro-3-chlorobenzene and about 2% of trifluoromethyltrichlorodifluorobenzene, is withdrawn From the fractionating column.

19.5 kg of trifluoromethyltrifluorodichlorobenzene are obtained. The yield of the target product is 92.8% for the starting trichloromethylpentachlorobenzene.

Example 9

Synthesis of 1-Trifluoromethyl-2,4,5,6-tetrafluoro-3-chlorobenzene

The process is carried out similarly to Example 1. The reactor is charged with 20 kg of trifluoromethylpentachlorobenzene, 19 kg of potassium fluoride, 0.75 kg of hexapropylguanidium chloride and 5 kg of products of incomplete fluorination of trifluoromethylpentachlorobenzene. The reaction mixture is agitated at a temperature of 180–190° C., and a fraction with a boiling point of 135–145° C., containing according to the GLC data 95% of 1-trifluoromethyl-2,4,5,6-tetrafluoro-3-chlorobenzene and 5% of 1-trifluoromethyl-2,4,6-trifluoro-3,5-dichlorobenzene, is withdrawn from the fractionating column.

14.2 kg of 1-trifluoromethyl-2,4,6-tetrafluoro-3-chlorobenzene are obtained. The yield of the target product is 88.7% for the starting trifluoromethylpentachlorobenzene.

Example 10

Synthesis of 1-Trifluoromethyl-2,3,4,5-tetrafluorobenzene

The process is carried out similarly to Example 1. The reactor is charged with 23 kg of 1-trifluoromethyl-2,3,4,5tetrachlorobenzene, 23 kg of potassium fluoride, 1 kg of hexaethylguanidium chloride and 10 kg or products of incomplete fluorination of trifluoromethyltetrachlorobenzene. The reaction mixture is agitated at a temperature of 170–180° C., and a fraction with a boiling point of 105–110° C., containing according to the GLC data 95% of 1-trifluoromethyl-2,3,4,5-tetrafluorobenzene and 5% of 1-trifluoromethyl-2,3,4-trifluoro-5-chlorobenzene, is withdrawn from the fractionating column.

16 kg of 1-trifluoromethyl-2,3,4,5-tetrafluorobenzene are obtained. The yield of the target product is 89% for the starting 1-trifluoromethyl-2,3,4,5-tetrachlorobenzene.

Example 11

Synthesis of Hexafluorobenzene

The process is carried out similarly to Example 1. The reactor is charged with 20 kg of hexachlorobenzene, 1.3 kg of N,N,N',N'-tetra-P-methylcyclohexyl-N"-methyl-N"-propylguanidinium chloride, 32 kg of potassium fluoride, and 11 kg of a mixture of products of incomplete fluorination of hexachlorobenzene ($C_6F_nCl_m$ where n=1–4, m=5–2). The reaction mixture is agitated at a temperature of 160–170° C., and a fraction with a boiling point of 80–85° C., containing according to the GLC data 91% of hexafluorobenzene and 9% of a mixture of products of incomplete fluorination, is withdrawn from the fractionating column.

11.7 kg of hexafluorobenzene are obtained. The yield of the target product is 88.6% for the starting hexachlorobenzene.

Example 12

Synthesis of Hexafluorobenzene

The process is carried out similarly to Example 1. The reactor is charged with 15 kg of hexachlorobenzene, 0.8 kg of N,N'diethyl-N",N"-di-n-propyl-phenylguanidinium chloride, 25 kg of potassium fluoride and 7 kg of a mixture of products of incomplete fluorination of hexachlorobenzene ($C_6F_nCl_m$ where n=1–4, m=5–2). The reaction mixture is agitated at a temperature of 160–170° C., and a fraction with a boiling point of 80–85° C., containing according to the GLC data 92% of hexafluorobenzene and 8% of a mixture of products of incomplete fluorination, is withdrawn from the fractionating column.

8.8 kg of hexafluorobenzene are obtained. The yield of the target product is 88.9% for the starting hexachlorobenzene.

Example 13

Synthesis of Pentafluorochlorobenzene

The process is carried out similarly to Example 1. The reactor is charged with 20 kg of hexachlorobenzene, 1 kg of N,N,N',N'-tetra-o-methylphenyl-N",N"-diethylguanidinium iodide, 26 kg of potassium fluoride and 14 kg of a mixture of products of incomplete fluorination of hexachlorobenzene. The reaction mixture is agitated at a temperature of 165–180° C., and a fraction with a boiling point of 117–118° C., containing according to the GLC data 88% of pentafluorochlorobenzene, 8% of hexafluorobenzene and 4% of a mixture of products of incomplete fluorination, is withdrawn from the fractionating column.

12.6 kg of pentafluorochlorobenzene are obtained. The yield of the target product is 88.1% for the starting hexachlorobenzene.

Example 14

Synthesis of Tetrafluorodichlorobenzenes

The process is carried out similarly to Example 1. The reactor is charged with 20 kg of hexachlorobenzene, 0.6 kg of N,N,N',N'-tetraethyl-N"-piperidinoguanidinium bromide, 21 kg of potassium fluoride and 7 kg of a mixture of products of incomplete fluorination of hexachlorobenzene. The reaction mixture is agitated at a temperature of 165–180° C., and a fraction with a boiling point of 150–152° C., containing according to the GLC data 89% of tetrafluorodichlorobenzene, up to 5% of chloropentafluorobenzene and more than 6% of trifluorotrichlorobenzene isomers, is withdrawn from the fractionating column.

13.7 kg of tetrafluorodichlorobenzene are obtained. The yield of the target product is 88.4% for the starting hexachlorobenzene.

Example 15

Synthesis of Octafluorotoluene

The process is carried out similarly to Example 1. The reactor is charged with 25 kg of trifluoromethylpentachlorobenzene, 1.4 kg of N,N'-di-morpholino-N"-ethyl-N"-butylguanidinium chloride, 29 kg of potassium fluoride and 10 kg of products of incomplete fluorination of trifluoromethylpentachlorobenzene ($C_6F_nCl_mCF_3$, n=1–3, m=4–2) The reaction mixture is agitated at a temperature of 150–170° C., and a fraction with a boiling point of 103–105° C., containing according co the GLC data 91% of octafluorotoluene and 9% of products of incomplete fluorination of trifluoromethylpenrachlorobenzene, is withdrawn from the fractionating column.

16.5 kg of octafluorotoluene are obtained. The yield of the target product is 88.2% for the starting pentachlorobenzene.

Example 16

Synthesis of Pentafluorobenzonitrile

The process is carried out similarly to Example 1. The reactor is charged with 25 kg of pentachlorobenzonitrile, 1.3 kg of N,N'-di-piperidino-N",N"-dipropylguanidinium. chloride, 34 kg of potassium fluoride and 12 kg of products of incomplete fluorination of pentachlorobenzonitrile. The reaction mixture is agitated at a temperature of 170–180° C., and a fraction with a boiling point of 160–163° C., containing according to the GLC data 92% of pentafluorobenzonitrile and 8% of products of incomplete fluorination, is withdrawn from the fractionating column.

15.7 kg of pentafluorobenzonitrile are obtained. The yield of the target product is 88.7% for the starting pentachlorobenzonitrile.

What is claimed is:

1. A process for preparing polyfluoroaromatic compounds by reacting corresponding halogen-containing aromatic compounds with an alkali metal fluoride in the presence of N,N'N"-hexa-substituted guanidinium halide as a catalyst, said reaction being carried out with heating in the medium of products of incomplete fluorination of said halogen-containing aromatic compounds and simultaneously a continuous withdrawal of the resulting target product being performed.

2. A process according to claim 1, wherein said N,N',N"-hexa-substituted guanidinium halide has the formula

wherein R—$R^3$=alkyl $C_1$–$C_7$, cycloalkyl $C_5$–$C_8$, aralkyl $C_7$–$C_{12}$; R and $R^1$ and/or $R^2$ and $R^3$ together with the nitrogen atom can form a heterocyclic residue, possibly containing one more heteroatom-oxygen or nitrogen; X=Cl, F, Br, I.

3. A process according to claim 1, wherein said withdrawal of the resulting target products is effected by fractionation.

4. A process according to claim 1, wherein said withdrawal of the resulting target products is effected by distillation.

* * * * *